United States Patent
Eder

(10) Patent No.: US 9,107,636 B2
(45) Date of Patent: Aug. 18, 2015

(54) SYSTEM FOR RECORDING ELECTRONEUROGRAPHIC ACTIVITY

(75) Inventor: Clemens Florian Eder, London (GB)

(73) Assignee: NEURODAN A/S, Aalborg SV (DK)

( * ) Notice: Subject to any disclaimer, the term of this patent is extended or adjusted under 35 U.S.C. 154(b) by 0 days.

(21) Appl. No.: 13/823,864

(22) PCT Filed: Sep. 26, 2011

(86) PCT No.: PCT/DK2011/050359
§ 371 (c)(1),
(2), (4) Date: Jun. 21, 2013

(87) PCT Pub. No.: WO2012/037946
PCT Pub. Date: Mar. 29, 2012

(65) Prior Publication Data
US 2013/0267816 A1 Oct. 10, 2013

(30) Foreign Application Priority Data
Sep. 24, 2010 (DK) .................... 2010 00861

(51) Int. Cl.
A61B 5/04 (2006.01)
A61B 5/00 (2006.01)
(Continued)

(52) U.S. Cl.
CPC ............ *A61B 5/4836* (2013.01); *A61B 5/04001* (2013.01); *A61B 5/6877* (2013.01); *A61B 5/7203* (2013.01); *A61F 2/72* (2013.01); *A61N 1/0504* (2013.01); *A61N 1/0551* (2013.01); *A61N 1/0556* (2013.01);
(Continued)

(58) Field of Classification Search
CPC ............ A61B 5/04001; A61B 5/4836; A61B 5/6877; A61B 5/7203; A61B 5/40; A61B 5/4851; A61B 2562/0209; A61N 1/36007; A61N 1/0504; A61N 1/0551; A61N 1/0556; A61N 1/36003; A61F 2/72
USPC ................. 600/26, 544; 607/48, 115–118
See application file for complete search history.

(56) References Cited

U.S. PATENT DOCUMENTS 4,448,202 A * 5/1984 Wajszczuk et al. .......... 600/522
4,543,956 A * 10/1985 Herscovici ...................... 607/13
(Continued)

FOREIGN PATENT DOCUMENTS

| EP | 1257318 | 11/2002 |
| WO | 9706728 A1 | 2/1997 |

(Continued)

OTHER PUBLICATIONS

Article entitled "A CMOS Adaptive Interference Reduction System for Nerve Cuff Recordings," Triantis et al.*
(Continued)

*Primary Examiner* — Rene Towa
(74) *Attorney, Agent, or Firm* — Holland and Hart

(57) ABSTRACT

A system for recording electroneurographic activity comprising at least three neurosense electrodes capable of sensing a nerve signal from a peripheral nerve and means for receiving and processing the sensed nerve signal to identify a signal indicative of a specific action being a movement of a body part performed by the patient and for producing a control signal in response thereto featuring means for rejection of signals originating from biological interference sources without affecting the electroneurographic activity measured.

14 Claims, 9 Drawing Sheets

(51) Int. Cl.
  *A61F 2/72* (2006.01)
  *A61N 1/05* (2006.01)
  *A61N 1/36* (2006.01)
(52) U.S. Cl.
  CPC ....... *A61N 1/36003* (2013.01); *A61N 1/36007* (2013.01); *A61B 5/40* (2013.01); *A61B 5/4851* (2013.01); *A61B 2562/0209* (2013.01)

(56) References Cited

U.S. PATENT DOCUMENTS

| | | | |
|---|---|---|---|
| 7,636,602 | B2 | 12/2009 | Baru Fassio et al. |
| 7,848,816 | B1 * | 12/2010 | Wenzel et al. ............... 607/42 |
| 7,896,808 | B1 | 3/2011 | Koh |
| 2003/0097050 | A1 * | 5/2003 | Baru Fassio ............... 600/345 |
| 2003/0144710 | A1 * | 7/2003 | Haugland et al. ........... 607/48 |

FOREIGN PATENT DOCUMENTS

| | | |
|---|---|---|
| WO | 0160445 A2 | 8/2001 |
| WO | 2011047381 A1 | 4/2011 |

OTHER PUBLICATIONS

Demosthenous, A., et al., "A Programmable ENG Amplifier with Passive EMG Neutralization for FES Applications," Circuits and Systems, 2008. ISCAS 2008. IEEE International Symposium on May 18, 2008, IEEE, Piscataway, NJ, USA, ISBN 978-1-4244-1683-7; ISBN 1-4244-1683-3.

Demosthenous, A., et al. "An ENG Amplifier with Passive EMG Neutralization," CONF: 2007 1 4th IEEE International Conference on Electronics, Circuits and Systems (ICECS '07), Dec. 11-14, 2007, Marrakech, Morocco, PUB: 2007 145h IEEE International Conference on Electronics, Circuits and Systems (ICECS '07), IEEE, Piscataway, NJ, USAIRN—ISBN 078-1-4244-137705, pp. 66-69.

Pachnis, I., et al., "Towards an Adaptive Modified Quasi-Tripole Amplifier Configuration for EMG Neutralization in Neural Recording Triples," 2010 IEEE International Symposium on Circuits and Systems. ISCAS 2010, 39 May to Jun. 2, 2010, Paris, France, PUB: 2010, IEEE International Symposium on Circuits and Systems. ISCAS 2010, IEEE, Piscataway, NJ, USA, ISBN 978-1-4244-5308-5, pp. 3144-3147.

Stein, R B., et al., "Principles Underlying New Methods for Chronic Neural Recording," The Canadian Journal of Neurological Sciences, Aug. 1975, pp. 235-244.

Andreasen, L. N. S., et al., "Artefact Reduction With Alternative Cuff Configurations," IEEE Transactions on Biomedical Engineering, vol. 50, No. 10, Oct. 2003, pp. 1160-1166.

Cole, K.S., et al., "Membrane Potential of the Squid Giant Axon During Current Flow," The Journal of General Physiology, Nov. 1, 1940, pp. 551-563.

Hoffer, J. A., et al., "Implantable Electrical and Mechanical Interfaces with Nerve and Muscle," Annals of Biomedical Engineering, vol. 8, 1980, Pergamon Press Ltd, pp. 351-360.

Rahal, M., et al, "An Improved Configuration for the Reduction of EMG in Electrode Cuff Recordings: A Theoretical Approach," IEEE Transactions on Biomedical Engineering, vol. 47, No. 49, Sep. 2000, pp. 1281-1284.

Stein, R. B., et al., "Predicted Amplitude and Form of Action Potentials Recorded from Unmyelinated Nerve Fibres," J. theor. Biol., vol. 32, 1971, pp. 539-558.

International Search Report for PCT International Application No. PCT/DK2011/050359, mailed Dec. 14, 2011, (4 pp.).

A. L. Hodgkin and W. A. Rushton, "The Electrical Constants of a Crustacean Nerve Fibre," Proc. R. Soc. Med. 134 (873): 444-479, 1946.

L. Hermann, "Untersuchungen ueber die Aktionsstroeme des Nerven: Teil II." Pfluger's Arch. Ges. Physiol. 24: 246-294, 1881 with Machine Generated Translation.

* cited by examiner

SYSTEM FOR RECORDING ELECTRONEUROGRAPHIC ACTIVITY

TECHNICAL FIELD

The present invention is generally concerned with the art of sensing neural signals from, and electrical stimulation of nerves. In particular it relates to amplification and filtering of neural signals in order to determine the best timing for initiating electrical stimulation of nerves.

BACKGROUND OF THE INVENTION

Electrical stimulation of nerve trunks and their branches is known to be effective in the treatment of a variety of neurological disorders in humans spanning from treatment of incontinence to gait disorders. Sensing and recording nerve signals is a discipline that aims for obtaining valuable input for actively controlling the timing of the electrical stimulation of nerves. The recorded nerve signals can also be used for controlling equipment placed outside the body as e.g. prostheses that serve as functional replacement of body parts.

When it comes to the art of electrical stimulation of nerves for the treatment of gait disorders, especially correcting dropfoot, electrodes are placed in the proximity of the peroneal nerve or its branches. An implantable pulse generator connected to the electrode generates a pattern of pulses to stimulate the nerve which will cause the foot dorsiflexor muscles to contract. Thus the foot will be lifted and it will be possible for the patient to swing the leg more naturally while walking. An example of a system for correction of drop-foot is known from EP 1 257 318 B1 to Neurodan A/S. The document covers the medical aspects and discloses examples of various preferred embodiments. For the triggering of the electrical stimulation of the nerve, according to the wanted reaction of the foot, the use of a heel switch is disclosed. The heel switch can be either connected to the pulse generator with electrical wires or it can include a wireless transmitter module for triggering the pulse generator. For the interface between the pulse generator and the electrode the system comprises an inductive link, an antenna to be mounted on the skin of the patient and a counterpart in form of an implantable antenna adapted to be implanted in the thigh of the patient. In a further embodiment it is shown that neural information recorded on e.g. the Sural nerve can be used for determining certain gait events such as heel strike and heel lift. For recording the neural information a nerve recording electrode is used, the nerve recording electrode in the preferred embodiment being a CUFF electrode, in principle a tube of insulating material with a number of contacts placed on the inside of the tube. The CUFF electrode is in one embodiment a multipolar nerve stimulation and recording electrode where the electrode is switched between a mode of recording nerve signals and a mode where electrical nerve stimulation is carried out. As can be seen in FIG. 1, natural sensors can be used as trigger input for a drop foot stimulator. Gait related information can be either sensed from a dedicated sensing electrode on a purely sensory nerve, or through the same electrode that the mixed common peroneal nerve (sensory and motor branches) is being stimulated with.

When it comes to recording information from natural sensors in living beings, information is encoded as action potentials, which are propagating along nerve fibers, either from their natural sensors, or to their muscles. An action potential is a transient change in the voltage between the intracellular (within the nerve fiber) and extracellular space (outside the nerve fiber) on either side of the membrane, as result of a mechanical, electrical or chemical stimulus that changes the electrochemical balance. This local disturbance can cause imbalance in the neighboring nerve tissue, allowing the action potential to propagate along the nerve. As a result of the short lasting disturbance at any given point on the nerve, ionic currents are flowing into and out of the membrane of the nerve cells. It is these membrane action currents, which allow the pickup of nerve activity with electrodes adjacent to the nerve, so-called extracellular electrodes.

If an electrode is placed on a cut nerve ending where the intracellular fluid makes good contact with restricted extracellular field, and a second electrode is placed further along the uninjured nerve, the shape of the extracellularly recorded action potential is identical to that of the membrane action potential at the second electrode [R. B. Stein and K. G. Pearson. amplitude and form of action potentials recorded from unmyelinated nerve fibres. J. Theoretical biology 32:539-558, 1971]. FIG. 2, shows the setup for a monopolar recording with an electrode placed around the nerve. The reference electrode is arranged far away from the recording electrode. Whenever the action potentials propagates under the electrode, the associated action currents causes voltage drops that can be picked up by the extracellular electrode. The voltage waveform approaches a scaled version of the action potential, with a scaling factor that depends on the transverse and longitudinal conductivity of the medium surrounding the nerve.

The monopolar configuration has the disadvantage that other biological interference as for instance caused by adjacent muscle activity will be indistinguishably picked up between recording and reference electrode. This situation can be greatly improved by recording nerve activity between two adjacent electrodes with an instrumentation amplifier which can greatly reduce any common mode interference as shown in FIG. 3. If the electrodes are aligned parallel to the gradient of the electric interference field, a tiny fraction of the greatly extended biological interference field can be sampled as differential voltage, which is increasing with the inter-electrode distance. But the inter-electrode distance cannot be made arbitrary small, because the wavelength of the action potentials increases with the nerve conduction velocity, and thus requires a larger inter-electrode distance for proper spatial sampling especially for fast conducting nerve fibers.

As previously mentioned, the amplitude of the action potentials recorded with an extracellular electrode is also dependent on the conductivity of the surrounding medium. It was found that the amplitude was proportional to the ratio between extracellular and axioplasmatic (i.e. the ohm'ic resistance inside of the nerve) resistivity [A. L. Hodgkin and W. A. Rushton. The electrical constants of a crustacean nerve fibre. Proc. R. Soc. Med. 134 (873):444-479, 1946].

Researchers have shown that if a nerve is brought into another electrically isolating medium like air (lifted the nerve with the attached hook electrode from the biological medium) or paraffin, the voltages significantly increase [L. Hermann. Untersuchungen ueber die Aktionsstroeme des Nerven: Teil II. *Pfluger's Arch. ges. Physiol.* 24:246-294, 1881], [K. S. Cole and H. J. Curtis. Membrane Potential of the Squid Giant Axon during current flow. *J. Gen. Physiol.* 24 (4):551-563, 1941]. This led researchers to the idea of surrounding the recording electrodes by an insulating silastic nerve cuff [R. B. Stein, D. Charles, L. Davis, J. Jhamandas, A. Mannard, and T. R. Nichols. Principles underlying new methods for chronic neural recording. *Canadian Journal of Neurological Sciences:*235-244, 1975], [J. A. Hoffer and G. E. Loeb. Implantable electrical and mechanical interfaces with nerve and muscle. *Ann. Biomed. Eng* 8:351-369, 1980].

These cuff electrodes can be produced by molding the electrode into silastic sheets that are wrapped around the nerve, and closed by a suture. As the silicone cuff is surrounding the recording electrodes, it also reduces the interference voltages between the two recording electrodes.

The interference can be further reduced by recording from a center electrode inside the cuff, against two short-circuited end electrodes [R. B. Stein, D. Charles, L. Davis, J. Jhamandas, A. Mannard, and T. R. Nichols. Principles underlying new methods for chronic neural recording. Canadian Journal of Neurological Sciences: 235-244, 1975]. This configuration is herein called quasi-tripolar, and shown in FIG. 4, where all previously mentioned recording configurations are depicted within a single sealed cuff electrode. The gradient of the electric field parallel to the nerve axis is slowly and monotonically changing. The connected end-electrodes measure the average of the distant source field at the ends of the recording zone, which is an estimate of the distance source field at the center electrode. Near field sources, such as action potentials within the nerve, are not monotonically changing, and thus the two end electrodes do not estimate the action potential at the center electrode. Thus, potential differences in the near field become differential mode, while those from distant sources become common mode. However, a residual differential interference cannot be avoided, due to the unobtainable perfect matching of all electrode- and inter-electrode impedances that would be required.

FIG. 5, shows that a bridge circuit may be chosen as a topology to describe the quasi-tripolar configuration when exposed to interference [M. Rahal, J. Winter, J. Taylor, and N. Donaldson. An improved configuration for the reduction of EMG in electrode cuff recordings: a theoretical approach. Biomedical Engineering, IEEE Transactions on 47 (9):1281-1284, 2000]. The model suggests that the output voltage is a product of both bridge voltage and a function of the mismatch between the tissue impedances between the electrodes (Rt1, Rt2) as well as the electrode-tissue impedances of the end electrodes Ze1 and Ze3. The later determine the amount of current that is flowing through the bridge wire, which always will be smaller than the total interference current flowing into the cuff. By bridge wire we refer to the (ideally) conducting wire that is connected between the end electrodes Ze1 and Ze3. If the end electrodes were perfect conductors with Ze1=Ze3=0 Ohm, all the interference current would flow through the bridge wire, and the bridge voltage would be zero. In that case, the mismatch of the impedances would not matter at all, and no interference voltage would appear at the output.

Unfortunately not all the interference current can be bypassed, due to the electrochemical properties of the electrode. The reactive parts of the electrode impedance can be decreased by proper surface treatment, but the access impedance is determined by the geometry of the contact disks as well as the amount of proliferated scar tissue encapsulating the contacts. Attempts were made to decrease the impedances of the end electrodes by adding additional electrodes, shorted together, as shown in FIG. 6. [L. N. S. Andreasen and J. J. Struijk. Artefact reduction with alternative cuff configurations 22. Biomedical Engineering, IEEE Transactions on 50 (10):1160-1166, 2003]. However, in comparison to the standard quasi-tripolar configuration, an improvement in the range between 18% and 24% was attributed to the decrease in end-electrode impedance.

The above described research overview is the basis for the design of the system granted in EP 1 257 318 B1 to Neurodan A/S which has been drawn up in the preamble of this application. The electrode design of the system works well both for sensing and stimulation. However, when it comes to sensing, a better separation of the signal from signals originating from biological interference sources as e.g. muscles would be appreciated.

DESCRIPTION OF THE INVENTION

It is an object of the present invention to provide an implantable system for sensing and recording of nerve signals which provides an improvement of nerve signal integrity and better separation of the nerve signal distinguishing it from the signals originating from other biological interference sources. Another object of the invention is to recognize specific patterns in the recorded nerve signal and provide an output signal that can be used as 1) a control signal for carrying out electrical nerve stimulation accordingly in order to activate certain muscle groups or 2) a control signal that can be used for controlling external equipment as e.g. prostheses that replaces body parts.

Concerning the interference signal, we may conclude that if the impedance mismatch, that caused the interference in the first place, cannot be compensated, the only reduction in interference can be achieved by decreasing the impedance of the end electrodes. Doing so will increase the by-passed interference current, reduce the bridge supply voltage and consequently the voltage between the center electrode and bridge wire.

The present invention aims to overcome the dependency of the by-passed interference current from the electrode impedances, by means of artificially creating a bypass current that is so high, that no more current is flowing between the recording electrodes, thus setting the bridge supply to zero. In this case all the interference current would flow over the bridge wire.

In a first aspect the invention provides: a system for recording electroneurographic activity comprising at least three electrodes, adapted to be placed along the longitudinal orientation of a peripheral nerve said electrodes capable of sensing a nerve signal and means for receiving and processing the sensed nerve signal activity and for producing a control signal in response thereto where the system has means for active rejection of signals originating from biological interference sources without affecting the measurement of electroneurographic activity.

It has to be understood that the mentioning of the cause of the nerve signal activity only serves for explaining the invention and for showing possible embodiments of the invention since the focus of the invention is put on the processing of nerve signals and rejection of interference signals. When it comes to specific use and embodiments of the invention, the identification of specific nerve signals is of interest, but depends to a large extent on the actual placement of the electrode on the nerve of interest. For sensing gait related nerve signals a suitable placement of the electrode could e.g. be on the sural, tibial or peroneal nerve. The causes for the nerve activity could be a result of a specific action as e.g. being a movement of a body part performed by the patient. However, the nerve signal activity could also originate from mechanic stimulation of the innervated skin areas which means that sensory nerves are being manipulated from an external source where the patient is not necessarily moving any body part. The cause of activation of the nerve is as such not limiting for the invention but merely points out the specific embodiment of the invention where the system is configured to identify a signal indicative of the specific action or specific sensory feedback.

More specifically the biological interference rejection is achieved by compensating the impedance of the end electrodes in order to provide a low-impedance shunt path for the interference source.

In order to facilitate a measurement of the signals originating from biological interference sources, an additional pair of electrodes can be arranged in the vicinity of the end electrodes for estimating the interference voltage between the end electrodes. Due to voltage drops caused by inter-electrode resistances, the accuracy of the estimated interference voltage will be higher, the closer this additional pair of electrodes is placed to the end electrodes.

In order to perform the measurement the system includes means for measuring the value of the biological interference voltage. In its simplest form the means for measurement could be an amplifier buffering the signal in order not to affect the signal but more sophisticated means as e.g. A/D converters could be foreseen. Using a A/D converter is especially advantageous if the system is equipped with a microcontroller, featuring recording of data and communication of data with external equipment, since the microcontroller will be able to calculate an appropriate signal to be used for providing a low-impedance shunt path for the interference source. Thus it will be possible for the microcontroller to record the wanted nerve signal from the center electrode without the impact of the biological interference sources since the signal contribution from this source has been balanced out.

For providing a feedback signal to be fed to the end electrodes in order to compensate the biological interference sources, the system is including a regulated bipolar current- or voltage source that based on the measured biological interference voltage applies a corresponding voltage or current of reverse polarity to the end electrodes. The generation of the control signal can be carried out in pure hardware or provided by a microcontroller processing control algorithms specified by portions of programming code stored in the memory of the microcontroller.

In another embodiment the feedback signal is provided by at least one negative impedance converter arranged in series with each end electrode. Thus a signal corresponding to the signal from the biological interference sources are provided with reverse polarity.

It will be appreciated if the impedance value of the negative impedance converter can be adjusted to partly or fully compensate the impedance of the end electrode. This can be done by arranging a set of discrete resistors and capacitors within a topology that closely resembles a model of the electrode impedance, and by choosing their values accordingly. Then it will be possible to choose the level of compensation of the biological interference voltage, which could be advantageous for creating a stable measurement system.

Especially it will be appreciated if the ratio between the actual end electrode impedance and the equivalent model impedance can be adjusted within a boundary that secures a stable operation, despite unpredictable end electrode impedance variations over time, following implantation. This will avoid that the negative impedance converter is causing the system to enter a state of self oscillation, keeping the system in a stable state.

The system is in one embodiment adapted to be implanted in the human or animal body.

An implantable system can be either designed in combination with an implantable pulse generator for nerve stimulation or as a standalone system for e.g. providing neural signals for the control of prostheses. The system will then be incorporated in the pulse generator for nerve stimulation or arranged in conjunction therewith.

The system for recording electroneurographic activity can thus be giving input to a system for correcting gait related deceases as e.g. drop-foot or a system for giving output signals for facilitating prostheses substituting body-parts as e.g. artificial legs or arms or a system for giving output to a system for treatment of incontinence. Another advantageous embodiment is in systems for sensing vagus nerve activity in order to detect the onset of epileptic seizures and to provide accordingly a control signal that can be used to moderate the effect of seizure.

More explicitly the recorded nerve signal can be used further for the control of systems for treatment of different diseases by the use of electrical stimulation of nerves as e.g. drop-foot where the peroneal nerve is stimulated for foot dorsiflexion.

Another use could be as a control signal for facilitating prostheses where a specific nerve signal could be isolated and amplified for controlling the movement of artificial limbs.

In a further embodiment, the system is giving input to a system for treatment of incontinence. Sustaining the unvoluntary emptying of the bladder can be done by electrical stimulation of the pudendal nerve or its afferents. Nerve signals recorded on the dorsal sacral nerve contains valuable information on the status of the bladder and can thus be used to determine if electrical stimulation has to be carried out or not.

The implantable electrodes could be carried out as single electrodes adapted to be placed in the vicinity of the nerve of interest and arranged in a way where a center electrode is surrounded by additional electrodes. A symmetric placement will be appreciated.

An electrode design carried out as a CUFF electrode is the preferred embodiment since this design seems to have the best qualities when it comes to electrical isolation from the biological interference sources, and yields neural signals of high amplitudes.

A preferred embodiment of the invention is featuring a CUFF electrode with more channels that could be equally spaced around the circumference. Each channel consists at least of three electrodes, one center and two end electrodes arranged in the longitudinal direction of the CUFF. The end electrode pair of one channel is configured or used to estimate the interference voltage, and feeding back a control signal of opposite polarity into the end electrodes of another neighboring channel.

The space between the additional electrode pair can be covered by electrodes other than the center electrode, because that space will be (ideally) free of any interference field. An assembly of a number of recording electrodes can be placed at arbitrary locations, either inside the single fascicles (intra-fascicular electrodes) or in-between the fascicles (inter-fascicular electrodes).

In another embodiment of the invention a medical lead with a number of electrodes is adapted to be placed along the longitudinal direction of the nerve so the principle as shown using the CUFF electrode design can be applied in respect to interference rejection. At least one electrode is arranged on the medical lead where additional electrodes are arranged otherwise inside the CUFF.

A medical lead as described could together with the nerve be enclosed by a CUFF. The CUFF could either include electrodes or purely serve as isolating media for the nerve and the medical lead.

DESCRIPTION OF THE DRAWING

Embodiments of the invention will be described with reference to the accompanying drawing, in which.

A first number of embodiments, not forming part of the invention but being useful for the understanding of the invention, has already been explained with reference to FIGS. 1 to 6 in the preamble of this application.

Figure 1:
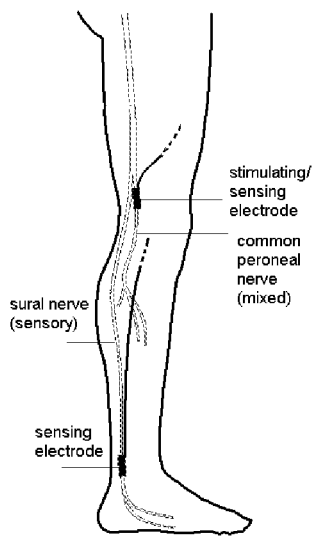
FIG. 1, shows an illustration of a leg region of a patient with dedicated electrodes implanted for recording nerves signals from the sural nerve, a purely sensory nerve. It also illustrates the placement of a cuff electrode placed on the peroneal nerve, for combined stimulation and sensing.
Figure 2:
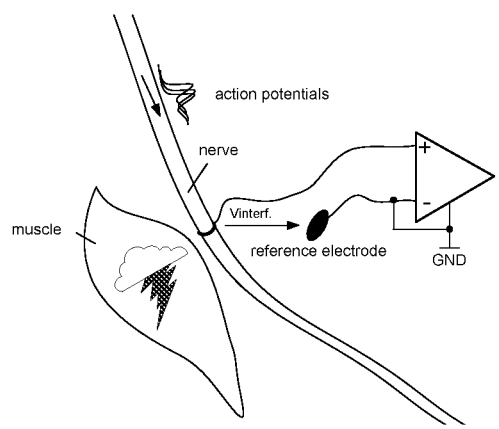
FIG. 2, shows a simplified illustration of a nerve for explanation of the problem of biological interference in monopolar recordings.
Figure 3:
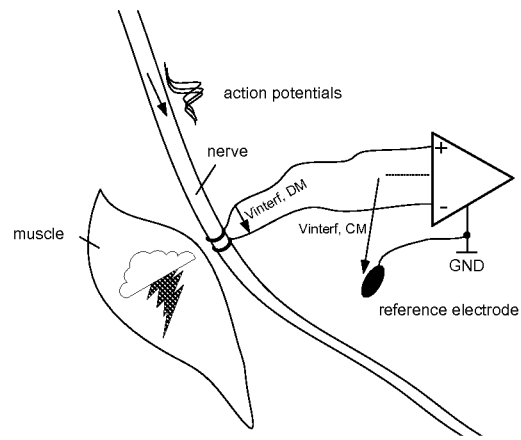
FIG. 3, shows a simplified illustration of a nerve for explanation of the problem of both common-mode and differential-mode interference voltages at the input of an instrumentation amplifier.
Figure 4:
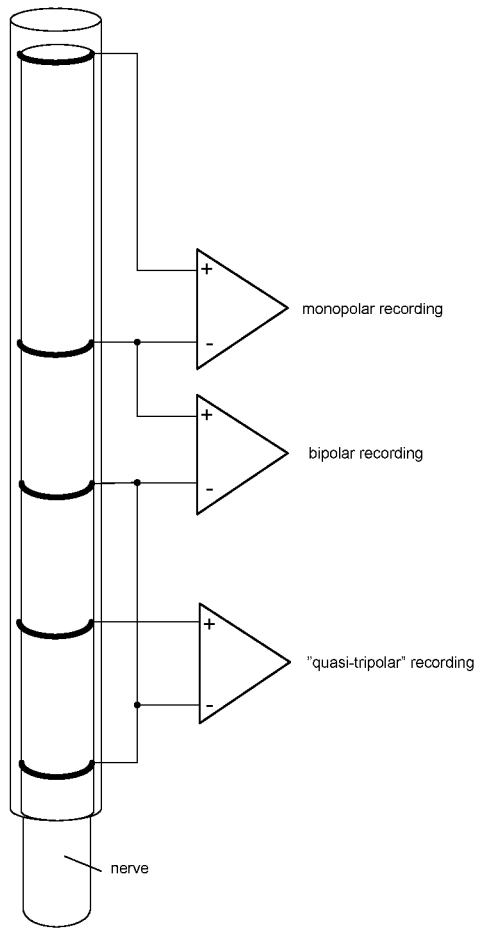
FIG. 4, shows typical configurations for recording neural activity in a sealed silastic CUFF electrode.
Figure 5:
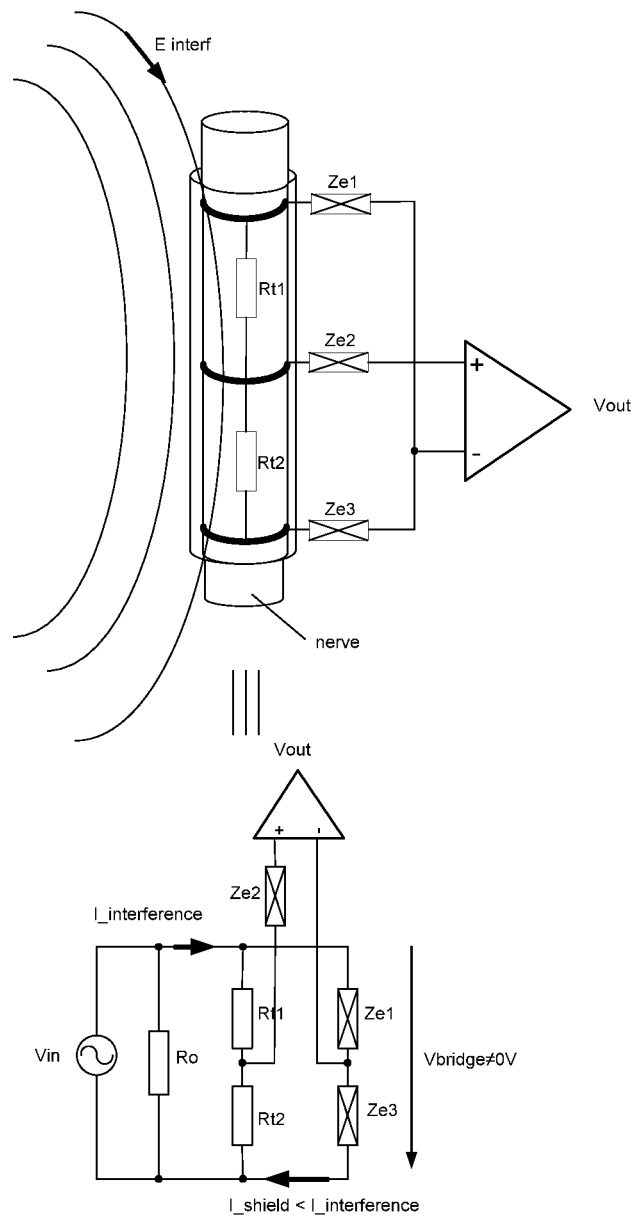
FIG. 5, is a schematic showing a representation of interference rejection by an equivalent circuit.
Figure 6:
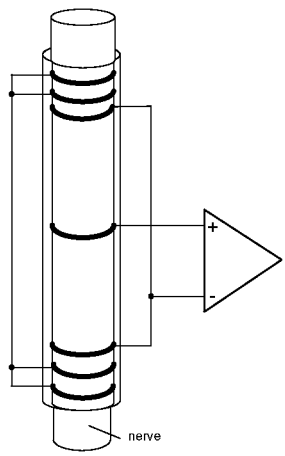
FIG. 6, shows an embodiment of an attempt to increase bypass current by adding additional end electrodes and shortening them together.

With a starting point in the description of the prior art, the present invention aims to overcome the dependency of the by-passed interference current from the electrode impedances, by means of artificially creating a bypass current that is so high, that no more current is flowing between the recording electrodes; referring to the bridge analogy in FIG. 5, this would mean that the bridge supply was set to zero. In this case the interference current would flow exclusively over the bridge wire.

Figure 7:
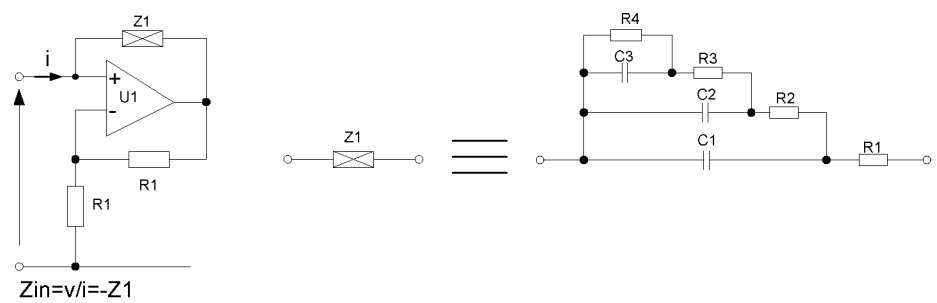
FIG. 7, shows the principle of a negative impedance converter.

One way to achieve this is by inserting a negative impedance converter (NIC) in series with each outer electrode. The NIC can be implemented by operational amplifiers (OPAMPs) and its principle is shown in FIG. 7. Herein the negative impedance converter is intended to invert the electrode impedance represented by Z. The frequency dependency of the electrode impedance can be obtained by measurements and the equivalent representation with a recursive RC structure can be used to accurately model the impedance. If the model accurately represents the impedance of the actual electrode connected to the input, the series impedance of electrode and NIC input terminal will exactly add up to zero. In practice, an error due to mismatch, $\Delta Z$, has to be tolerated.

Figure 8:
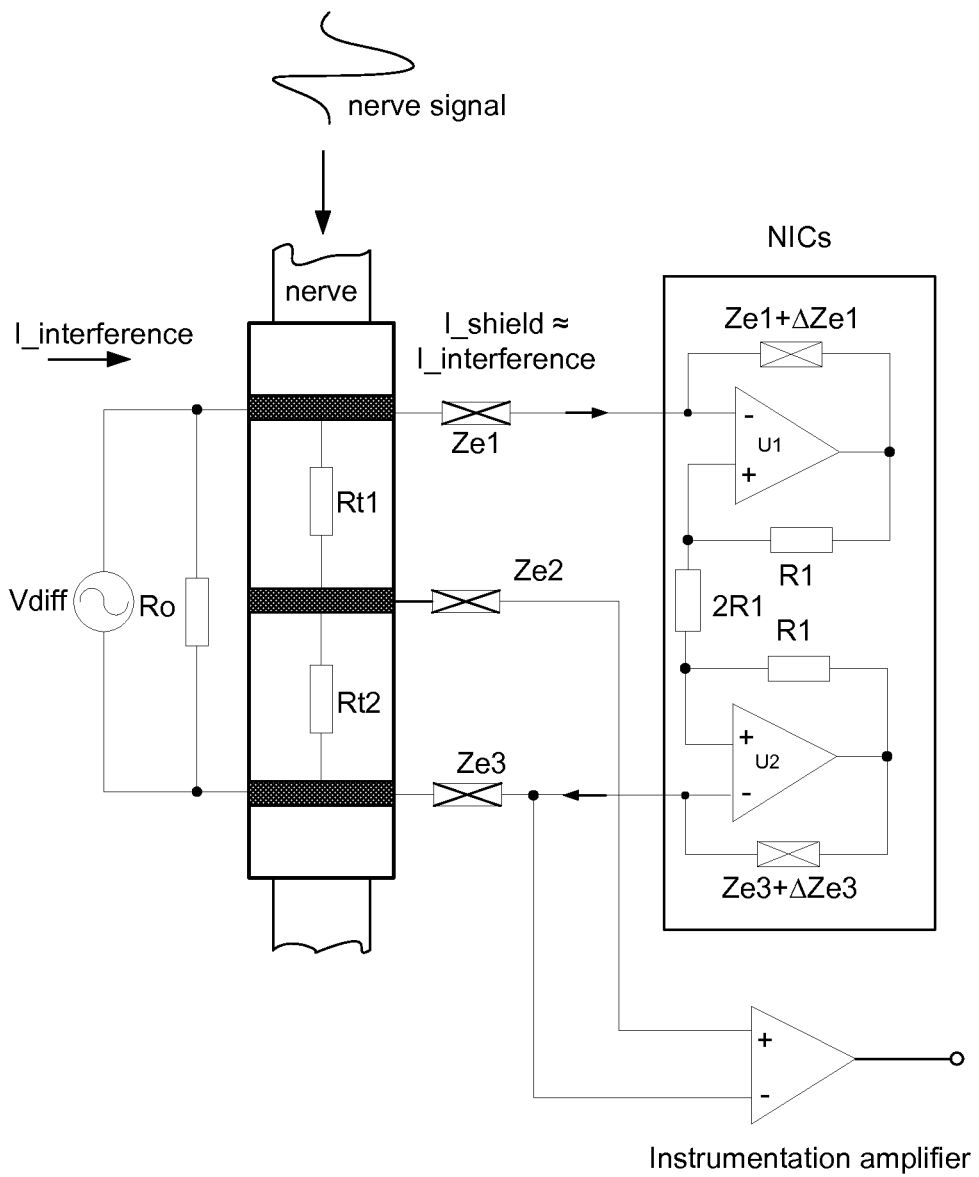
FIG. 8, shows an application of a system for recording of nerve signals with two NIC's in series with the electrode impedances.

This error can be chosen such that a stable operation can be guaranteed despite variations within the electrode type, as well as gradual variations as time goes by after implantation. The invention is using two NICs in series with the electrode impedances, in order to create a resulting impedance close to zero, and therefore to create a perfect short circuit, in which most of the interference current will run through the outer electrodes; thus, the interference voltage is minimized. As recognized in FIG. 8, the voltage over 2R1 has opposite polarity from the voltage over Ro, and currents through the impedances Ze1 and Ze3 can be higher than in the case of a bridge wire.

Figure 9:
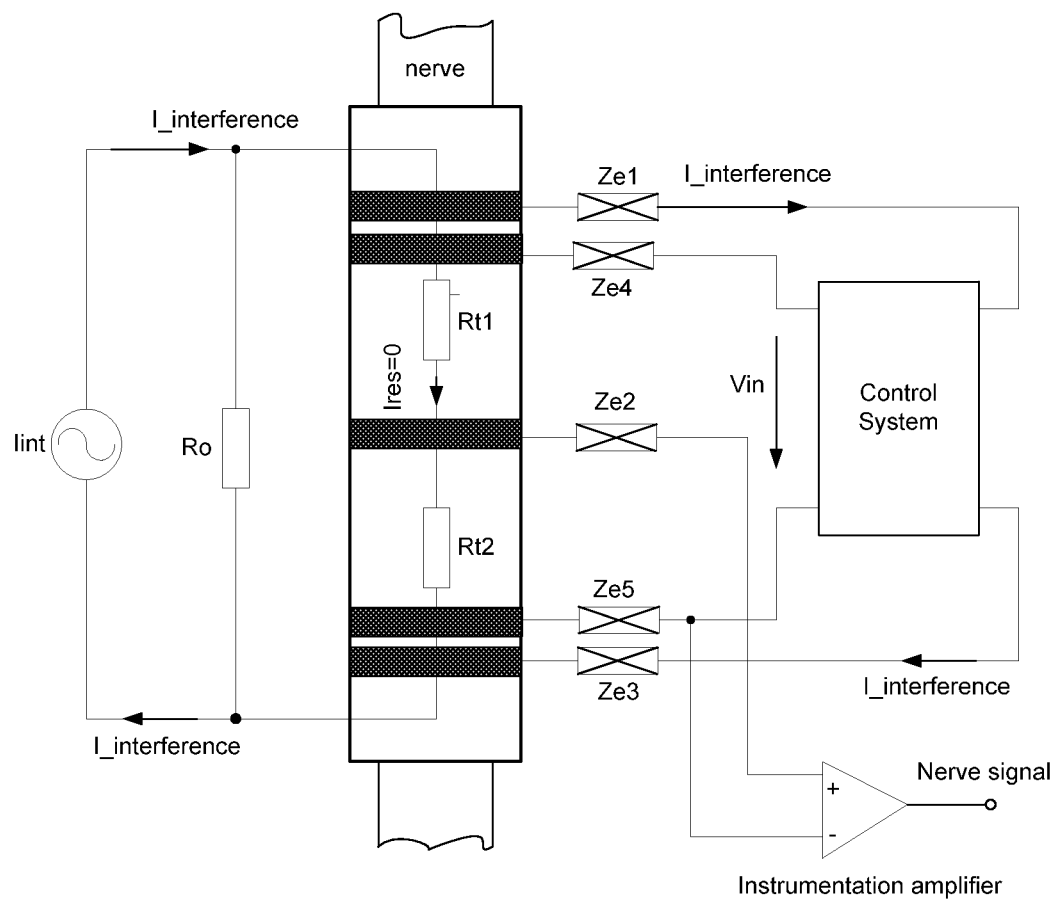
FIG. 9, shows an application of a system for recording of nerve signals with an additional pair of electrodes for measurement of the value of the signal that origins from biological interference sources.

Another way of achieving a perfect short circuit is to measure the voltage between the outer electrodes by means of an extra pair of electrodes, and using either a regulated bipolar current- or voltage source to increase the interference current over the outer electrode, until the measured voltage approaches zero. This principle is shown in FIG. 9.

Both methods are based on the assumption that neither the intervention with the NIC, nor the application of the control circuit has an influence on the nerve signal, which is the signal of interest. The outer electrodes are kept at the same potential, but this does not have an effect on the recorded nerve signal, as long as the inter-electrode distance is long enough to allow spreading of the waveform at a certain point in time. The situation is basically the same as for the outer electrodes being short circuited by wire. However, with the help of the present invention, the inter-electrode distance can be made arbitrary large without affecting the picked up interference.

Figure 10:
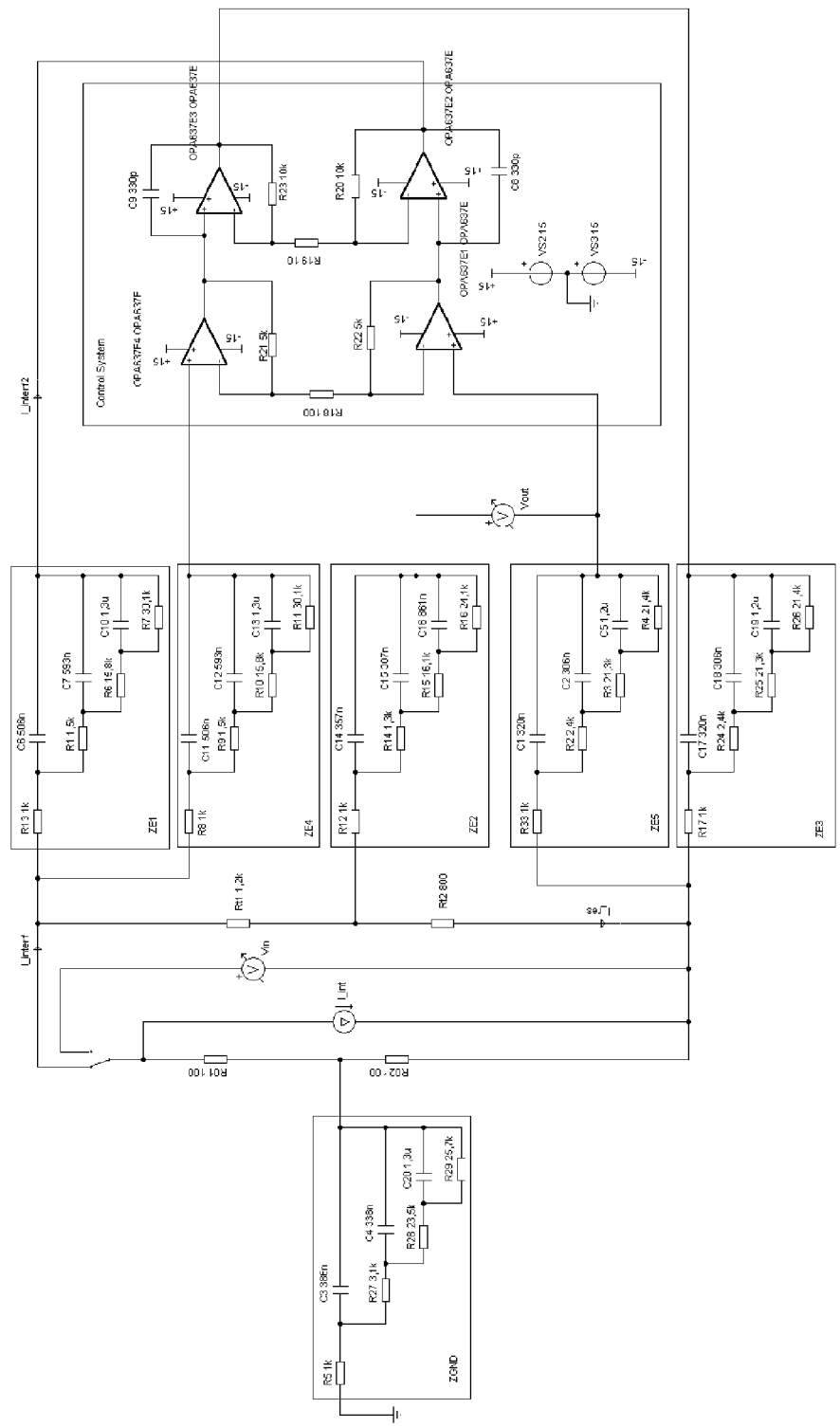
FIG. 10, shows the simulated circuit representing the simplified illustration in FIG. 9, FIG. 11, shows a simulated frequency sweep with reference to the input voltage.

To test this principle in greater detail, a realistic circuit simulation was performed using the program TINA (Design-Soft, Inc.). The electrodes were implemented as RC networks, whose values were obtained from an equivalent circuit model that tightly fitted previously performed electrode impedance. To account for electrode impedance variations, the values for the end and additional end electrodes were chosen according to three out of ten fitted models that deviated the most among each other. In addition, the inter-electrode resistances were chosen 1.2 kOhm and 800 Ohm. For the control system, the simulated OPAMPs OPA637E were part of differential mode amplifiers, as shown in FIG. 10.

Figure 11:
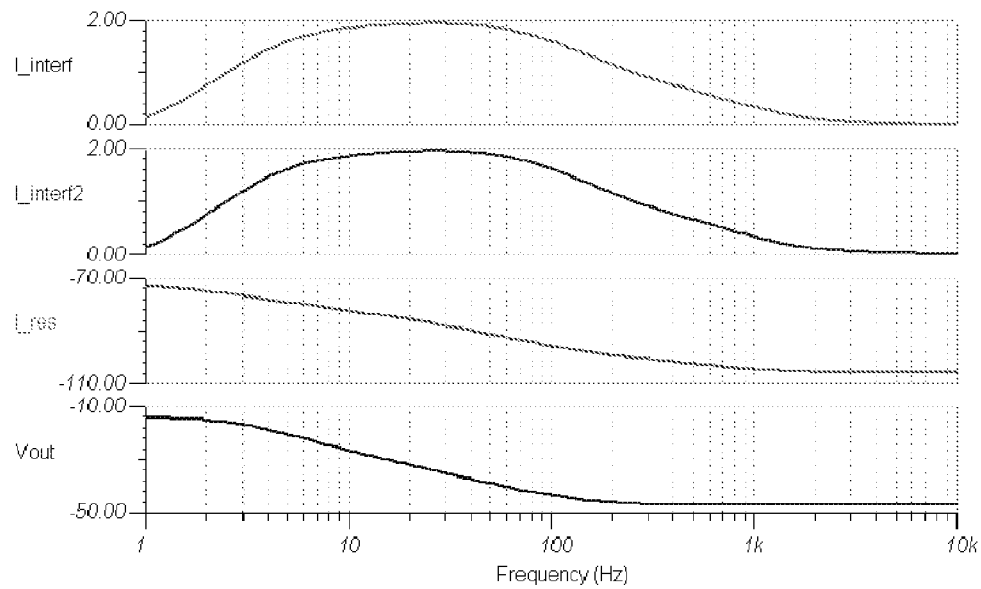

The interference rejection performance was quantified by a frequency sweep of the interference current source and the measurement of the output voltage (between center and outer electrode) with respect to the voltage that would have been measured without intervention (FIG. 11). That voltage is dampened at the output to about 43 dB at 100 Hz. Note that almost all the interference current flows through the control system, and that this current has only a 2 dB dependency on the frequency on the frequency. According to the current divider rule, a tiny residual current of −96 dB at 100 Hz is equivalent to a 12 MOhm resistor connected in parallel to the interference source, and not 2 kOhm. This indicates that the simulated control system shows indeed excellent performance in shunting interferential sources.

Figure 12:
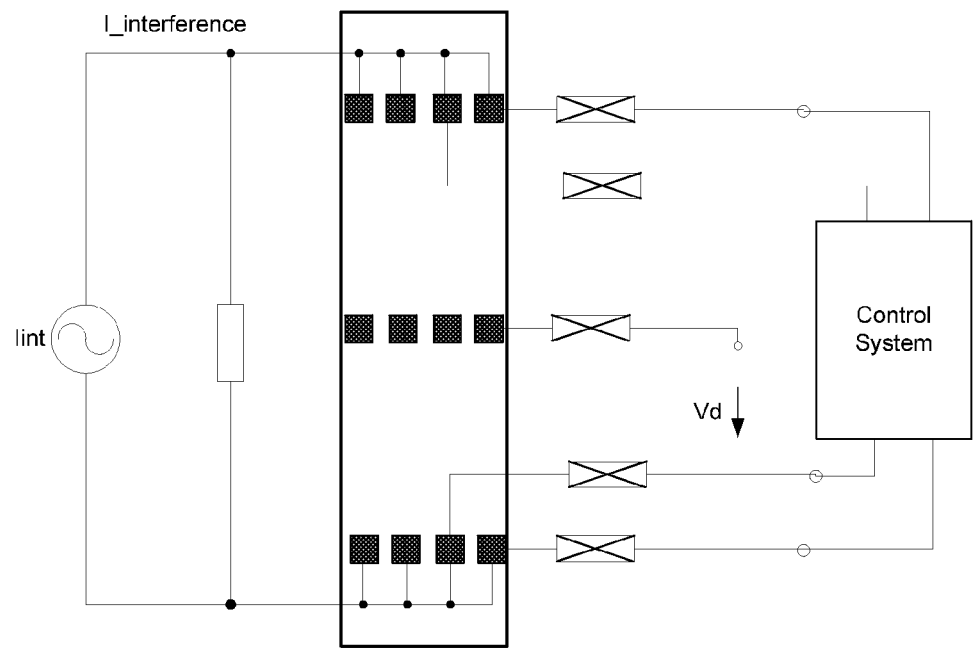
FIG. 12, shows a multipolar cuff electrode where the additional electrode pair is avoided by replacing it with the end-electrodes from a neighboring channel.

In a preferred embodiment the invention is applied on a multipolar CUFF electrode as shown in FIG. 12. The electrode consists of four channels that are equally spaced around the circumference. Each channel consists of three electrodes, one center and two end electrodes. In this preferred embodiment, the end electrode of one channel is used to estimate the interference voltage, and feeding back a control signal of opposite polarity into the end electrodes of another neighboring channel. The number of channels needed in the CUFF is at least two. However, a larger number than four could also be foreseen.

Figure 13:
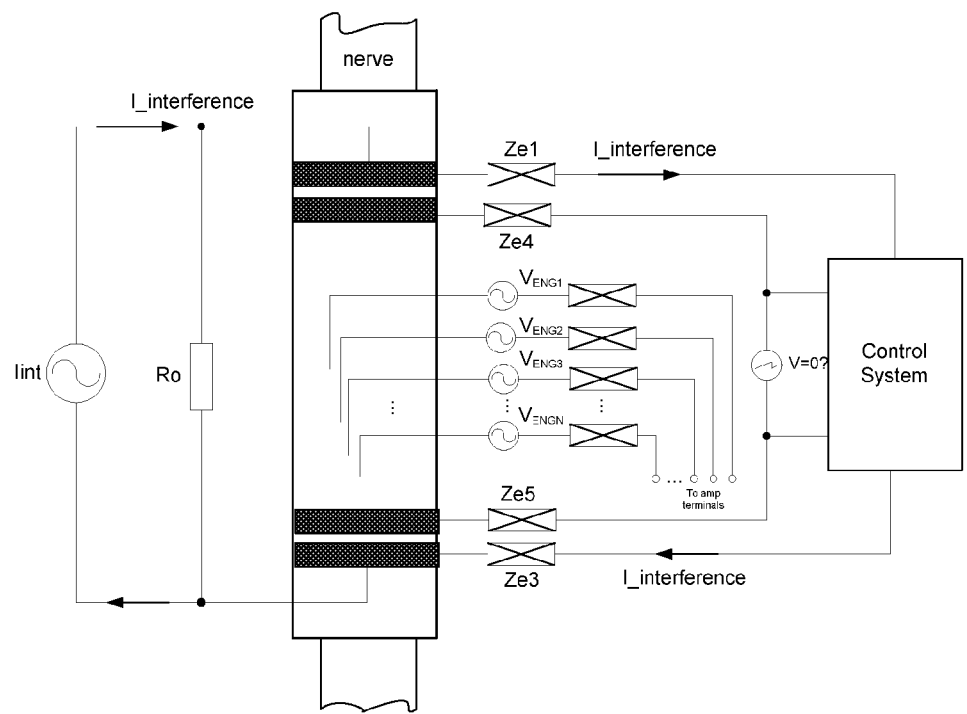
FIG. 13, shows an embodiment of a silastic cuff wrapped around the nerve with an arbitrary combination of recording electrodes between the end-electrodes

FIG. 13 shows an embodiment with a silastic cuff wrapped around the nerve, using the end-electrodes as well as an additional electrode pair for interference rejection as described. The space between the additional electrode pair Ze4 and Ze3 can be covered by electrodes other than the center electrode, because that space will be (ideally) free of any interference field. The drawing indicates an assembly of a number recording electrodes that can be placed at arbitrary locations, either inside the single fascicles (intra-fascicular electrodes) or in-between the fascicles (inter-fascicular electrodes). The invention works with any types of recording electrodes between Ze4 and Ze5.

Figure 14:
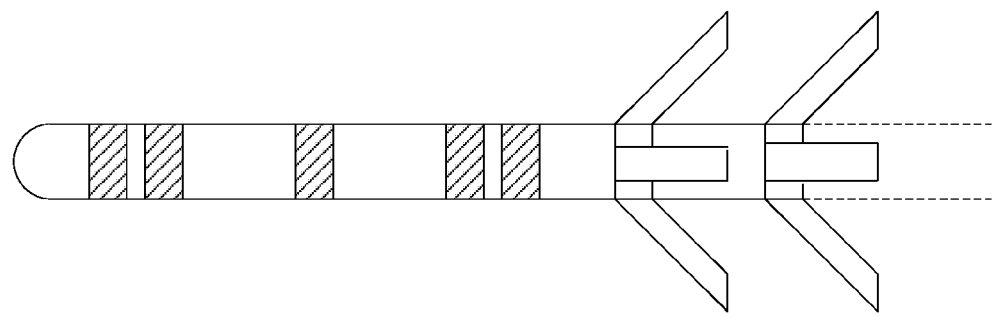
FIG. 14, shows the electrode arrangement carried out as a medical lead.

FIG. 14 shows an embodiment of the invention where a medical lead that is adapted to be placed along the longitudinal direction of the nerve is used for sensing electroneurographic activity. As can be seen the lead features the 5 electrodes, so the principle as shown using the CUFF electrode design can be applied in respect to interference rejection. The use of a medical lead can be of advantage in situations where the anatomical location does not allow the surgical implantation of a cuff electrode, such as in the central nervous system or in the genital areas.

In a special embodiment not shown, deriving from the embodiment shown in FIG. 13, a medical lead is placed in the longitudinal direction of the nerve and is, together with the nerve, enclosed by a CUFF. In one embodiment the CUFF could include electrodes. In another embodiment the CUFF includes no electrodes and serves purely as isolating media for the nerve and the medical lead.

It will be appreciated if the invention is not limited to the embodiments of the electrodes presented. The CUFF could be made of a silastic material into which the electrode terminals are incorporated. The electrodes could also be arranged on a mesh before being molded into a flexible sheet of silastic material.

It will be appreciated if the invention also includes other embodiments of medical leads and monopolar as well as bipolar electrodes that can be used for carrying out the invention.

The invention claimed is:

1. A system for recording electroneurographic activity, comprising:
   at least three electrodes, adapted to be placed along the longitudinal orientation of a peripheral nerve, said electrodes including end electrodes and a center electrode positioned between the end electrodes, the electrodes being capable of sensing a nerve signal, the end electrodes being connected to each other;
   a control device comprising at least one circuit and being configured to measure a differential interference voltage between the end electrodes, receive and process the sensed nerve activity between the center electrode and one or more of the end electrodes, and produce a control signal in response thereto for controlling an external device;
   a regulated bipolar current or voltage source that, based on the differential measured interference voltage between the end electrodes, applies a corresponding differential voltage or current of reverse polarity to the end electrodes to cancel the interference voltage, between the end electrodes without canceling nerve signals measured between the center electrode and one or more of the end electrodes such that the system actively rejects signals originating from biological interference sources that are separate from the sensed nerve signal without affecting a measurement of electroneurographic activity.

2. A system according to claim 1, wherein an additional pair of electrodes is arranged in the vicinity of the end electrodes.

3. A system according to claim 1, wherein the system includes at least one negative impedance converter arranged in series with each end electrode.

4. A system according to claim 3, wherein an impedance value of the at least one negative impedance converter is adjustable to partly or fully compensate the impedance of each end electrode.

5. A system according to claim 4, wherein a ratio between an actual end electrode impedance and an equivalent model impedance can be adjusted within a boundary that secures operation, despite unpredictable impedance variations in the end electrodes over time.

6. A system according to claim 1, wherein the system is adapted to be implanted in a human or animal body.

7. A system according to claim 1, wherein the electrodes in the system are arranged inside a cuff with a plurality of channels, each channel comprising at least three electrodes that include one center and two end electrodes arranged in the longitudinal direction of the cuff, the end electrodes of one channel are configured to estimate the interference voltage, and the system is configured to provide and feedback the interference voltage with opposite polarity into the end electrodes of another neighboring channel.

8. A system according to claim 1, wherein the system is incorporated in an implantable pulse generator for electrical nerve stimulation.

9. A system according to claim 8, wherein the system is specially adapted for providing input to a system for correcting gait related diseases.

10. A system according to claim 8, wherein the system is specially adapted for providing a control signal for facilitating prostheses where a specific nerve signal is isolated and amplified for controlling the movement of artificial limbs.

11. A system according to claim 8, wherein the system is specially adapted for providing an input signal to a system for treatment of incontinence.

12. A system according to claim 1, wherein at least one of the electrodes is arranged on a medical lead adapted to be placed along the longitudinal direction of the nerve.

13. A system for recording electroneurographic activity while rejecting signals originating from biological interference sources that are separate from the sensed nerve signal without affecting the measurement of electroneurographic activity, said system comprising:
   a plurality of electrodes adapted to be placed along a longitudinal orientation of a peripheral nerve and configured to sense a nerve signal, the plurality of electrodes including end electrodes connected to each other and a center electrode positioned between the end electrodes;
   a control device configured to:
      measure a differential interference voltage of biological interference sources between the end electrodes;
      receive and process the sensed nerve activity between the center electrode and one or more of the end electrodes;
      produce a control signal in response to said sensed nerve activity for controlling an external device;
   a regulated bipolar current or voltage source operable to apply a corresponding differential voltage or current of reverse polarity to the end electrodes to cancel the interference voltage between the end electrodes without canceling nerve signals measured between the center electrode and one or more of the end electrodes, the differential voltage or current of reverse polarity being based on the differential interference voltage of the biological interference sources measured between the end electrodes.

14. A system according to claim 13, wherein the plurality of electrodes includes at least two pairs of electrodes.

\* \* \* \* \*